United States Patent
Vissers et al.

[11] Patent Number: 5,814,742
[45] Date of Patent: Sep. 29, 1998

[54] FULLY AUTOMATED MICRO-AUTOSAMPLER FOR MICRO, CAPILLARY AND NANO HIGH PERFORMANCE LIQUID CHROMATOGRAPHY

[75] Inventors: Johannes Petrus Cornelis Vissers; Jean-Pierre Chervet, both of Amsterdam, Netherlands; Pierre Salzmann, San Francisco, Calif.

[73] Assignee: L C Packings, Nederland B.V., Amsterdam, Netherlands

[21] Appl. No.: 729,388

[22] Filed: Oct. 11, 1996

[51] Int. Cl.$^6$ .................. G01N 1/10; G01N 1/18
[52] U.S. Cl. .................. 73/863.73; 73/863.72; 73/864.21; 73/864.83; 73/863.82; 73/64.56
[58] Field of Search .................. 73/864.21, 864.83, 73/864.86, 863.81–863.86, 863.72, 863.73, 863.02, 863.01, 64.56, 864.11, 864.81

[56] References Cited

U.S. PATENT DOCUMENTS

| | | | |
|---|---|---|---|
| 3,849,070 | 11/1974 | Garza et al. | 73/863.85 |
| 4,429,584 | 2/1984 | Beyer et al. | 73/864.21 |
| 4,620,452 | 11/1986 | Seki | 73/864.21 |
| 4,713,974 | 12/1987 | Stone . | |
| 4,756,201 | 7/1988 | Uffenheimer | 73/864.21 |
| 4,836,038 | 6/1989 | Baldwyn . | |
| 4,939,943 | 7/1990 | Strohmeier . | |
| 4,957,009 | 9/1990 | Nohl et al. | 73/864.84 |
| 5,297,431 | 3/1994 | White | 73/864.22 |
| 5,400,666 | 3/1995 | Song | 73/864.21 |
| 5,431,067 | 7/1995 | Anderson et al. . | |

OTHER PUBLICATIONS

Simpson (1995) J. Chromotogr. A, 691, 163–170, "Modification of a conventional high–performance liquid chromatography autoinjector for use with capillary liquid chromatography".

Cortes et al. (1992) J. Chromatogr. 607, 131–134, "Quantitative reproducibilty study with automated microcolumn liquid chromatorgraphy".

J. Vissers, J.P. Chervet and J.P. Salzmann, Int. Lab., Jan. 1996., "A fully automated microautosampler for micro and capillary liquid chromatography".

*Primary Examiner*—Hezron E. Williams
*Assistant Examiner*—Nashmiya Fayyaz
*Attorney, Agent, or Firm*—Richard Aron Osman

[57] ABSTRACT

A liquid chromatography micro-autosampler is disclosed that permits the sampling of very small samples quantities at high accuracy, while minimizing extracolumn band broadening. The autosampler employ a sample intake tubing connected to the injection valve, that is further connected to an aspirating device. The intake tubing terminates within the hollow bore of a needle which is used to penetrate sample containers. Improved injection profiles are obtained by minimizing injection plug dispersion with back flushing of the injection plug and a low dispersion injection routine and extremely small sample quantities can be handled with a micro pick-up injection routine.

12 Claims, 5 Drawing Sheets

FULLY AUTOMATED MICRO-AUTOSAMPLER FOR MICRO, CAPILLARY AND NANO HIGH PERFORMANCE LIQUID CHROMATOGRAPHY

BACKGROUND

Field of the Invention

The field of the invention is autosamplers and autoinjectors for high performance liquid chromatography.

Introduction

Packed capillary high-performance liquid chromatography (HPLC), also referred to as capillary, or micro HPLC, provides for analytical separations with limited solvent and analyte consumption, enhanced resolution, and ease of interface with mass spectrometry (for review, M. Saito, K. Hibi, D. Ishii and T. Takeuchi, in D. Ishii, Eds., "Introduction to Microscale High Performance Liquid Chromatography", VCH Publishers, 1988). The technology is widely used in biochemical analysis (e.g. Lewis et al. (1991) Anal. Chem, 66, 585). However, to penetrate additional fields of application, such as routine drug analysis, capillary HPLC must be capable of unattended automated operation.

Current available HPLC autosamplers are not suitable for automated micro- and nanoliter injections, e.g. Anderson et al. U.S. Pat. No. 5,431,067; Strohmeier, U.S. Pat. No. 4,939,943; Baldwyn, U.S. Pat. No. 4,836,038 and Stone, U.S. Pat. No. 4,713,974. Some autoinjectors are compatible with micro or capillary LC but lack the capacity to handle minute sample and are not able to perform automated variable micro- and nanoliter injections. For example, Simpson (1995) J. Chromotogr. A, 691, 163, describes the conversion of a conventional LC autosampler into a micro-autosampler, though the extracolumn band broadening and required sample sizes were high. Similar results were reported with the use of an automated air driven 100 nl internal rotor injection valve dedicated for single sample capillary LC (Cortes et al. (1992) J. Chromatogr. 607, 131).

Ideally, a micro-autosampler for micro and/or capillary LC should be able to handle both small (e.g.<100 nl) and large injection volumes (e.g.>5 $\mu$L) without showing any peak dispersion and should be flexible in injecting different sample volumes from multiple different samples. Furthermore, the micro-autosampler should be able to handle minute sample volumes with minimal sample loss and should not contribute to extracolumn band broadening.

Aspects of this invention are disclosed in J. Vissers, J. P. Chervet and J. P. Salzmann, Int. Lab., January 1996.

SUMMARY OF THE INVENTION

The invention provides methods and apparatuses for automated sampling of liquid samples for chromatography. A particular disclosed micro-autosampler permits the sampling of very small samples quantities at high accuracy, while minimizing extracolumn band broadening. The micro-autosampler is particular useful in micro, capillary and nano HPLC, but is also applicable to any other analytical technique that requires automated handling of minute samples or the introduction of ideal plug profiles such as in fast HPLC separations using non-porous packing materials and/or columns packed with very small particles.

The autosampling methods and apparatuses employ sample intake tubing connected to an injection valve, that is further connected to an aspirating device—e.g. a syringe—allowing minute sample volumes to be handled much easier than with previous injection devices. The intake tubing terminates within the hollow bore of a needle which is used to penetrate sample containers (e.g. septum-covered containers). After penetration, the intake tubing can slide within the bore to safely reach the sample.

The disclosed methods and apparatuses also offer improved injection profiles by minimizing injection plug dispersion with back flushing of the injection plug and a low dispersion injection routine. With the low dispersion injection routine, the injection valve is switched back to its load position after a period of time defined by the injection volume and the flow rate of the mobile phase. In this way undesired extracolumn band broadening effects like incomplete sample recovery—as caused by insufficient flow characteristics—are minimized.

Extremely small sample quantities can be handled with a micro pick-up injection routine. The first step in the micro pick-up injection routine consist of filling the fused silica needle with mobile phase or another suitable liquid. After the sample is introduced into the sample loop, a second plug of solvent is aspirated to sandwich the sample between two solvent plugs. Hence, all of the sample from the loop is loaded onto the micro, capillary or nano HPLC column with minimal sample loss.

DETAILED DESCRIPTION OF THE INVENTION

Figure 1:
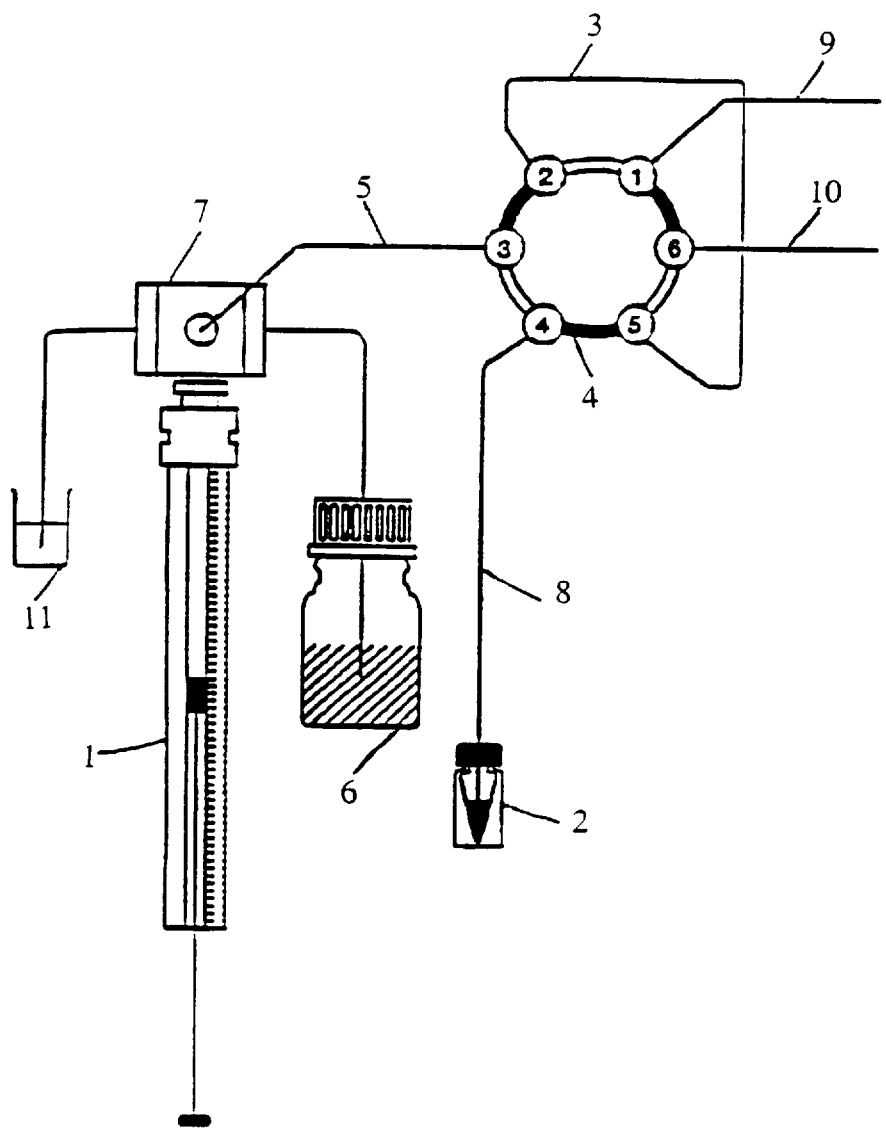
FIG. 1. Schematic of an apparatus for sample intake in micro, capillary and nano HPLC; the FAMOS™ microautosampler.

A scheme of a micro-autosampler according to the invention is given in FIG. 1. The micro-autosampler uses a high precision sample aspirating device 1 to aspirate the sample from a vial 2 into a sample loop 3 (or an internal loop or volume element) of a multiport injection valve 4. To avoid contamination of the sample aspirating device 1, the micro-autosampler is equipped with a transfer tubing 5 between the sample aspirating device and the injection valve 4. The transfer tubing 5 can thus function as a buffer tubing to avoid contamination of the sample aspirating device 1. A wash solvent containing bottle 6, connected to the sample aspirating device 1 and the transfer tubing 5 via a low pressure valve 7, is used to flush any of the sample from the transfer tubing 5 and the sample intake tubing 8, and to rinse both rigorously. The injection valve 4 is further connected to a pump lead 9 and a column lead 10, and the low-pressure valve 7 is further connected to a waste reservoir 11.

The autosampler allows for fully automated injections of any volume ranging from 25 nl to 5 μL without the need for sample loop 3 exchange, simply by programming the desired injection volume. The precision of the injection is determined by the displacement of sample liquid by the sample aspirating device 1. Injection volumes larger than 5 μL are easily accessible by installing a larger sample loop 3, a larger transfer tubing 5, and a larger sample aspirating device 1.

Figure 2C:
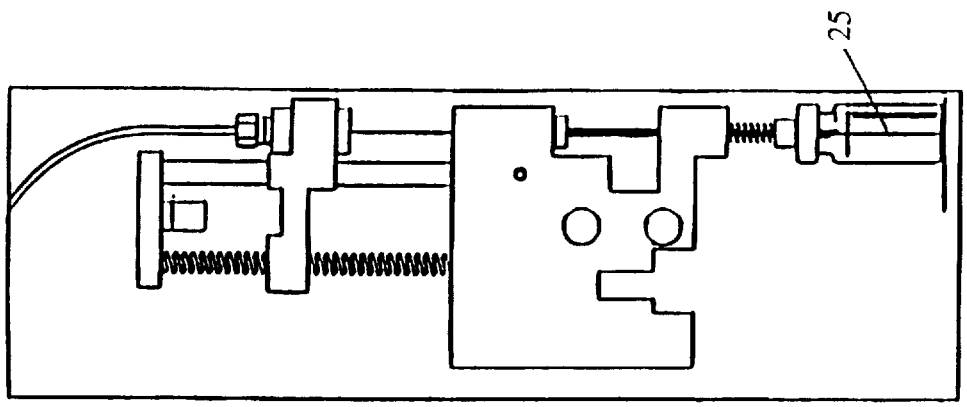
FIG. 2. Schematic of a sample injection system describing the needle movement. (A) initial position, (B) puncturing of the vial septum by the needle and applying head space pressure, and (C) insertion of the fused silica injection needle.
Figure 2B:
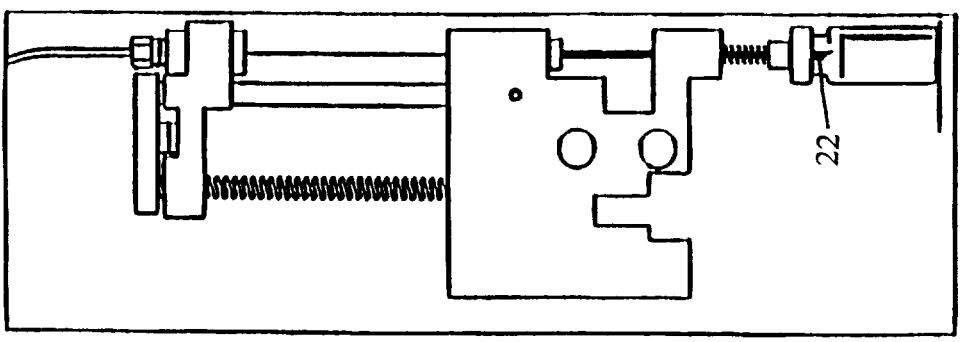
Figure 2A:
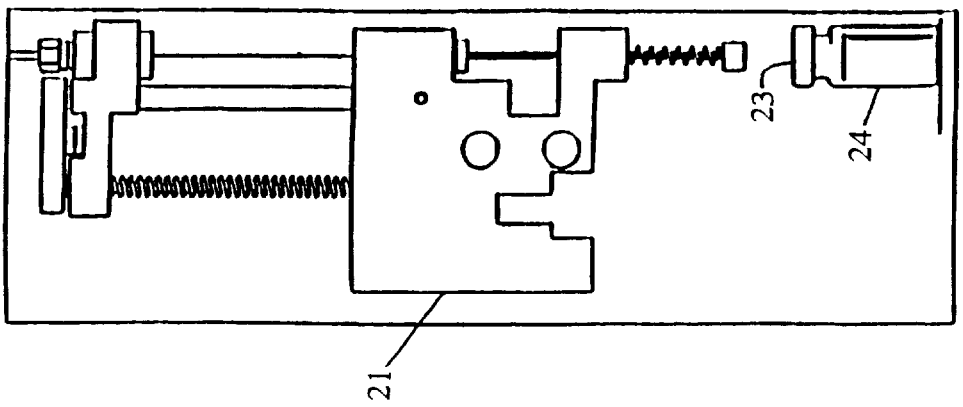

A schematic representation of the sample uptake mechanism of the micro-autosampler is given in FIG. 2. The micro-autosampler uptake unit 21 uses a separate hollow pre-puncturing needle 22 to pierce the septum 23 of the tapered micro sample vial 24, which allows for the protected insertion of a fused silica capillary sample intake tubing 25 through the hollow pre-puncturing needle 22 and the septum 23 to the bottom of a sample vial 24. Consequently, extremely small sample volumes can be processed without any metal contact. The depth of insertion can be defined by the operating software. Optionally, head space pressure can be applied on the sample to facilitate the aspiration of viscous and volatile samples, and to enhance injection reproducibility.

Small volume sample injections can be performed in different ways, including full loop fill, partial loop fill and the disclosed micro pick-up method to transport the sample into the loop of the injection valve. The sources of dispersion are for all injection methods the same: dispersion of the injection plug—that is extracolumn band broadening originating from the injection valve and any other components that may get in contact with the sample are caused by: the Poiseuille flow profile, the flow rate of the mobile phase, dead volumes that may act as mixing devices, the viscosity and density differences between the sample solvent and the mobile phase, the geometry of the flow paths, and the roughness of the wetted surfaces.

Figure 3A:
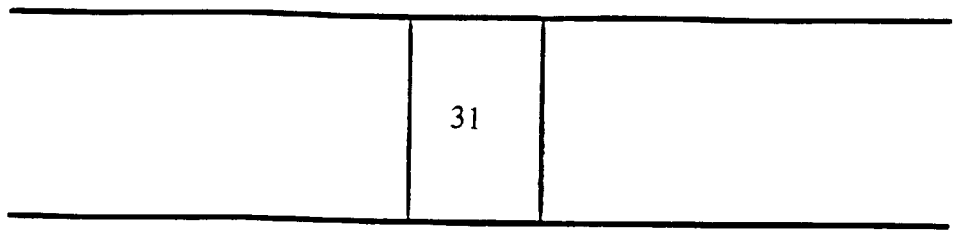
FIG. 3. Schematic representation of different types of injection profiles: (A) ideal injection plug profile, (B) practically obtained Poiseuille like injection profile, and (C) injection profile with the disclosed autosampler using back flushing and the low dispersion injection routine.
Figure 3B:
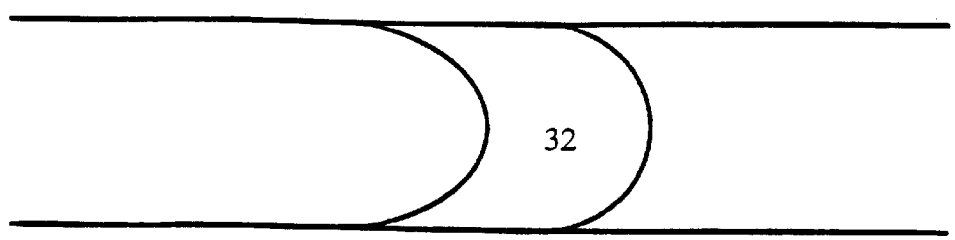
Figure 3C:
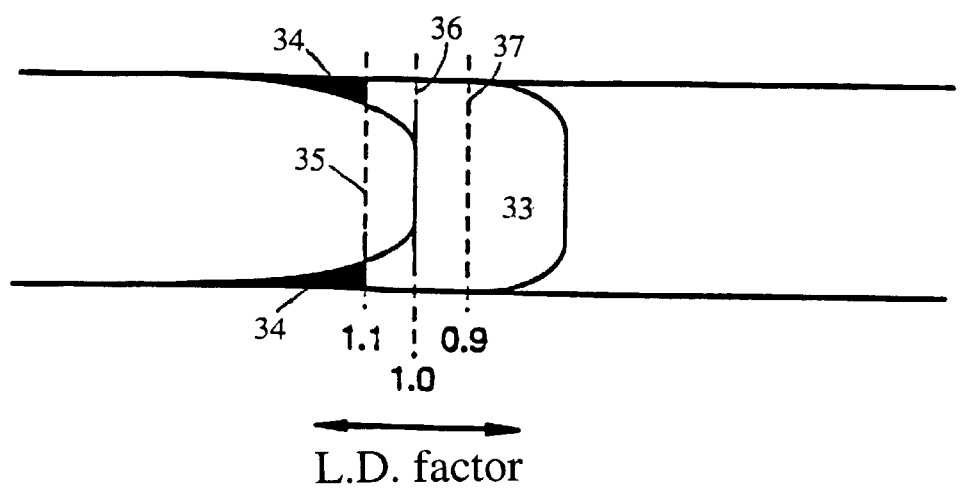

Ideally, an injection plug should be rectangular shaped 31, as shown in FIG. 3a. However, the injection profiles 32 that are practically obtained using prior art methods, see FIG. 3b, are—due to the above described band broadening processes—not well defined. However, injections performed with the disclosed micro-autosampler using the backflush mode and a low dispersion injection routine result in almost ideal injection profiles 33, FIG. 3c. By switching the valve back to the load position the injection is terminated, consequently, the undefined tailing part 34 of the injection plug is cut away and guided to waste. The time at which the injection valve is switched back to the load position—as indicated by the dashed lines 35, 36 and 37 in FIG. 3c for three different switching times—is dependent on the sample volume and flow rate of the mobile phase and can be controlled by operating software. In this case, the switching time $S_t$ may be calculated automatically by the instrument using the following formula:

$$S_t = f \times V_{inj} \times 60/F$$

where f is the low-dispersion factor, $V_{inj}$ the sample injection volume in microliters, and F the volumetric flow rate in microliters per minute. The only parameters that have to be entered into the autosampler are the flow rate, injection volume and the low dispersion factor, typically 1.1. Hence, for an injection volume $V_{inj}$ of 1 microliter and a flow rate F of 5 μL/min—using a switching factor of 110%, i.e. f=1.1—the instrument calculates an $S_t$ value of 13.2 s.

To determine the dispersion of the sample in the injection valve the peak asymmetry of the compounds that are eluting from the analytical column was measured. Since the detector signal represents the overall band broadening of the chromatographic system, it is easily possible to study extracolumn band broadening—originating from the injection valve—by keeping all other parameters that may contribute to extracolumn band broadening constant.

The following examples are offered by way of illustration and not by way of limitation.

EXAMPLES

All capillary LC experiments were performed with a conventional HPLC pump (model PU-980, Jasco, Tokyo, Japan), a microflow processor (model IC-70-CAP, LC Packings, Amsterdam, The Netherlands), 15 cm×300 mm i.d. Fusica columns packed with octadecyl modified silica particles with a nominal diameter of 5 μm (model FUS 15-05-C18, LC Packings), and a UV-VIS absorbance detector (model UV-975, Jasco) equipped with an 8-mm, 35 μL U-shaped capillary flow cell (model UZ-JAS-CAP, LC Packings). Injection of the samples into the micro-LC stream were carried out with the micor-autosampler using a low dead volume six-port valve (VICI AG Valco Europe, Schenkon, Switzerland). UV absorbance detection was at 254 nm.

The mobile phase consisted of 70:30 (v/v) $CH_3CN$ in $H_2O$ (unless otherwise stated) and was delivered to the column through the microflow processor at a flow rate of approximately 4 μL/min. A low-pressure in-line filter (0.2-μm disposable filter, Whatman Inc., Clifton, N.J.) was placed between the mobile-phase reservoir and the pump to prevent contamination or clogging of the capillary LC system. Peak dispersion, reproducibility, and linearity studies were conducted with a reversed-phase test mixture containing uracil (4.3 μg/mL), naphthalene (57.5 μg/mL), biphenyl (4.60 μg/mL), fluorene (8.21 μg/mL), anthracene (9.85 μg/mL), and fluoranthene (26.3 μg/mL).

Carryover and micro-pickup experiments were performed with the reversed-phase test mixture or with a test sample containing thiourea and caffeine. Solvents and solutes of both test mixtures were purchased from Fluka AG (Buchs, Switzerland). Data acquisition was performed with MT-2 chromatography software (Kontron Instruments, Milan, Italy).

Equipment to test extracolumn injection dispersion consisted of a conventional HPLC system that was converted into a capillary HPLC system with the use of modular components [J. E. Battersby, et al., Anal. Chem., 67 (1995) 447; S. K. Chowdhury, et al., Anal. Chem. 67 (1995) 390—398; and J. Roboz, et al., Rapid Commun. Mass Spectrom., 8 (1994) 621].

Figure 4A:
FIG. 4. Comparison of 200 nl injections performed with (A) a micro injection valve and (B) the disclosed micro-autosampler. Separations were carried out on a 15 cm×300 micron I.D. column packed with 3 micron C18 particles. Solutes in order of elution: (1) uracil, (2) naphthalene, (3) biphenyl, (4) fluorene, (5) anthracene, (6) fluoranthene.
Figure 4B:
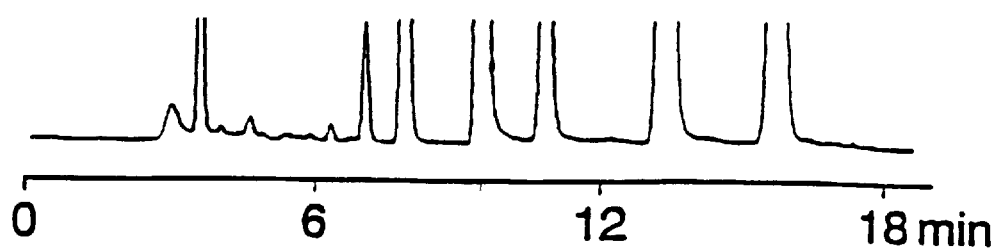

The micro-autosampler was compared with a 200 nl internal loop micro injection valve. The results are given in FIG. 4. The upper trace of FIG. 4 shows the test chromatogram using the micro injection valve. The lower trace show the chromatogram using the micro-autosampler and the Low Dispersion Injection routine. The results in FIG. 4 clearly show much better injection profiles using the autosampler with the programmable injection algorithm. For example, the peak asymmetry of the last eluting peak was equal to 1.25 for the micro injection valve and 1.05 for the micro-autosampler. Using the low dispersion algorithm for large volume injections of 5 μL, the peak asymmetry could even be reduced from 1.40 down to 1.05.

The linearity of injection of the micro-autosampler was determined by injecting different sample volumes of the reversed phase test mixture and subsequent evaluation of the peak height and peak area of the eluting chromatographic bands. Samples volumes larger than 200 nl were diluted in 20:80 (v/v) $CH_3CN$ in $H_2O$ to prevent exceeding of the linear range of the detector and mass over load of the micro column. The linearity of injection in the tested range of 25 nl to 5 μL was excellent with a squared correlation coefficient better than 0.9995 for the peak height and better than 0.9998 for the peak area measured on fluoranthene The reproducibility of the injection was tested using Flow Injection Analysis (FIA) and Capillary LC. In the FIA mode the reproducibility of the injection was conducted with 100 nl (partial loop fill) and 5 μL (full loop) injections. Twenty-five consecutive injections were performed to determine the relative standard deviation (RSD) of the micro-autosampler. For the 100 nl partial loop fill injections RSD values of 0.6% were found and for the 5 μL full loop injections the RSD values were equal to 0.4%.

Figure 5:
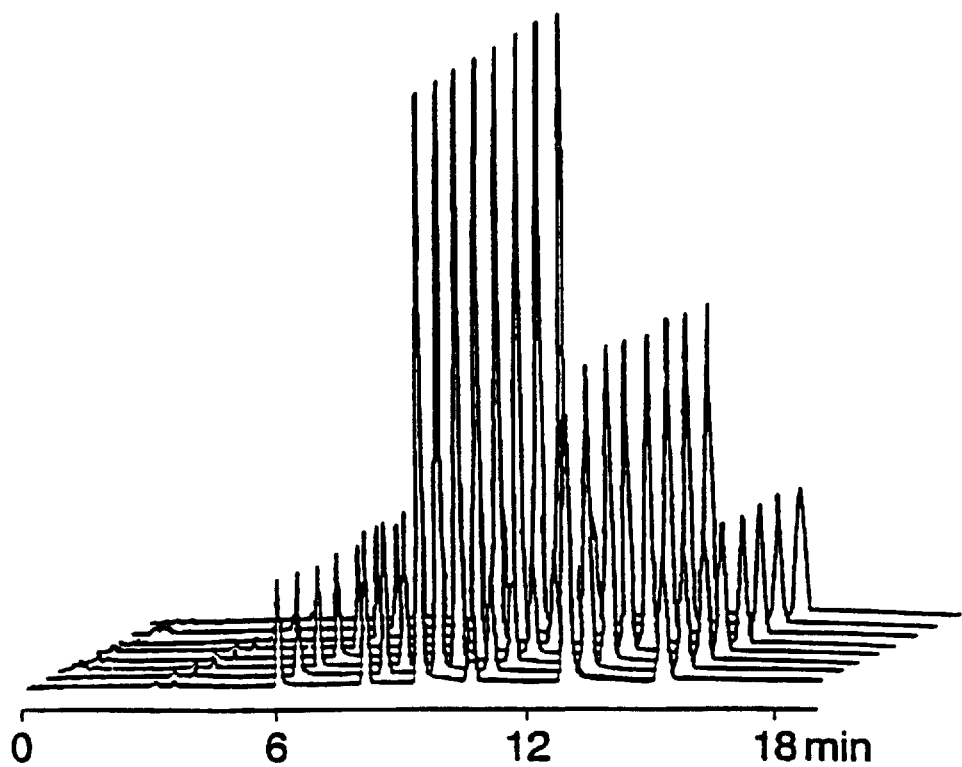
FIG. 5. Consecutive chromatographic separations of a polyaromatic hydrocarbon test mixture (injection volume 200 nl).

In FIG. 5 eight consecutive separations of the polynuclear aromatic hydrocarbon test mixture (injection volume 200 nl) are depicted to demonstrate the chromatographic reproducibilities under capillary LC conditions. Conditions were as described for FIG. 4.

The carryover of a chromatographic system is dependent of the type of components that are studied, that is adsorbing vs. non-adsorbing compounds. For typical dead volume markers like uracil and thiourea, the carryover—with an additional programmed needle wash—of<0.025% was found using FIA, independent of the volume or concentration of the injected sample. Carryover experiments were also conducted with the polynuclear aromatic hydrocarbon mixture, which contains compounds that are known to adsorb on the surface of stainless steel tubing and rotor. For small volume injections of 100 nl no carryover was observed, that is the peaks were too small to be detected in the base line noise. For large volume injections of 5 μL the average total chromatographic carryover with programmed needle wash was<0.1% for the PAH mixture.

Micro pick-up injections (Micro Sampling) of very small sample volumes are feasible due to the fused silica sample intake tubing. The first step in the micro pick-up consist of filling of the sample intake tubing and the removal of wash solvents by aspirating the mobile phase—or a solvent with lower solvating strength than the mobile phase—from a transport liquid vial. Next, the sample intake tubing moves to the sample vial and aspirates the programmed injection volume. After that, the sample intake tubing moves back to the transport liquid vial to aspirate mobile phase. By performing injections in this manner, the sample is quantitatively transported into the loop of the injection valve without sample loss.

Micro pick-up experiments were conducted with uracil and caffeine. The mobile phase consisted of 35:65 (v/v) $CH_3CN$ in $H_2O$ and the flow rate was 4 μL/min. The peak height and peak area were compared with a calibration curve which was determined in a similar manner to the micro pick-up experiments. The results of the micro pick-up experiments are given in Table 1.

TABLE 1

Recoveries obtained for uracil and caffeine with the micro-pick up injection routine

| Injection Volume (μL) | Sample Volume (μL) | Uracil Recovery | Caffeine Recovery |
|---|---|---|---|
| 1 | 2 | 1.03 | 1.03 |
| 1 | 1 | 0.92 | 0.96 |
| 0.5 | 1 | 0.84 | 1.02 |
| 0.5 | 0.5 | 0.74 | 0.90 |

Nearly complete recovery was obtained for 1 μL injections of uracil and caffeine, that is injecting 1 μL out of a total sample volume of 1 or 2 μL. For injections of 1 μL out of 1 μL sample only 4–8% is lost, which is most likely caused by adsorption effects off the investigated compounds onto the surface of the vial, sample intake tubing, rotor seal of the injection valve, the loop of the injection valve or the tubing. Taking all these possible adsorption effects into consideration, the recovery can be regarded as excellent. Handling 500 nl samples worked very well for caffeine—only 10% loss of sample when 500 nl is injected out of 500 nl—and somewhat lower recoveries were obtained for uracil.

Besides uracil and caffeine, the PAH mixture was used to evaluate the micro pick-up injection routine. The recovery for these type of components was determined by injecting 1 μL of the PAH test mixture out of a total sample volume of 5 μL, and by injecting 1 μL out of a total sample volume of 1 μL. The recovery for the micro pick-up injection mode for the PAH compounds is almost equal to 100% for injections of 1 μL out of 5 μL, and approximate 80% for injections of 1 μL out of 1 μL sample; favorable recoveries given the absorbing nature of PAH compounds.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An autosampler for use in liquid chromatography comprising:

a) means for sample uptake by inserting a sharpened tip of a needle comprising a bore through a septum of a septum-covered sample container and into said container, translocating a sample intake tube comprising a terminus through said bore from a first position wherein said intake tube terminus is recessed within said needle to a second position wherein said terminus protrudes from said tip and into said sample, and aspirating a measured aliquot of less than about 5 μL of said sample into said intake tube to form an injection plug of said sample;

b) means for sample bracketing by bracketing said injection plug of said sample between first and second solvent plugs of a chromatographic mobile phase liquid;

c) means for reducing band dispersion by time-controlled switching of a multiport injection valve through which said injection plug is transferred, said injection plug being separated into more dispersed and less dispersed portions, whereby said less dispersed portion is directed to a chromatographic column and said more dispersed portion is diverted from said chromatographic column; wherein the time at which the injection valve is switched back to a load position and injection is terminated, the switching time $S_t$ is calculated using the formula:

$$S_t = f \times V_{inj} \times 60/F$$

where f is a low-dispersion factor, $V_{inj}$ is the desired sample injection volume in microliters, and F is the volumetric flow rate in microliters per minute.

2. An autosampler according to claim 1, wherein said aliquot has a volume less than about 100 nl.

3. An autosampler according to claim 1, wherein said controlled switching is fully automated and effected by an algorithm.

4. An autosampler for use in liquid chromatography comprising:

a sample aspirating device, a low pressure valve, a transfer tube, a multiport injection valve with an electronically time-controlled valve switch, a sample intake tube, a needle, means for translocating said needle, means for translocating said intake tube, and a chromatographic column;

wherein said aspirating device and said transfer tube are in low pressure valve-regulated liquid communication, said intake tube and said transfer tube are in injection valve-regulated liquid communication, and said intake tube is concentric with and internal to said needle, wherein said needle translocating means introduces said needle into a septum-covered container, said intake tube translocating means slides said intake tube through said needle into said container without contacting said septum, wherein said aspirating device transfers less than about 5 μL of said sample into and through said sample intake tube to said injection valve, whereby said sample separates into more dispersed and less dispersed portions; and, wherein said valve switch directs said less dispersed portion to said chromatographic column and diverts said more dispersed portion from said chromatographic column, wherein the time at which the injection valve is switched back to a load position and injection is terminated, the switching time $S_t$ is calculated using the formula:

$$S_t = f \times V_{inj} \times 60/F$$

where f is a low-dispersion factor, $V_{inj}$ is the desired sample injection volume in microliters, and F is the volumetric flow rate in microliters per minute.

5. An autosampler according to claim 4, wherein said valve switch is fully automated and controlled by an algorithm.

6. An autosampler according to claim 4, wherein said sample has a volume less than about 100 nl.

7. A method for automated sampling of a portion of a liquid sample for liquid chromatography, said sample contained in a septum-covered sample container, said method comprising steps:

a) inserting a sharpened tip of a needle comprising a bore through said septum and into said container, b) translocating a sample intake tube comprising a terminus through said bore from a first position wherein said intake tube terminus is recessed within said needle to a second position wherein said terminus protrudes from said tip and into said sample, c) aspirating a measured aliquot of less than about 5 μL of said sample into said intake tube to form an injection plug of said sample;

d) transferring said injection plug to a time-controlled multiport injection valve whereby said injection plug separates into more dispersed and less dispersed portions; and, e) switching said valve whereby said less dispersed portion is directed to a chromatographic column and said more dispersed portion is diverted from said chromatographic column, wherein the time at which the injection valve is switched back to a load position and injection is terminated, the switching time $S_t$ is calculated using the formula:

$$S_t = f \times V_{inj} \times 60/F$$

where f is a low-dispersion factor, $V_{inj}$ is the desired sample injection volume in microliters, and F is the volumetric flow rate in microliters per minute.

8. A method according to claim 7, wherein said switching is fully automated and effected by an algorithm.

9. A method according to claim 7, wherein said terminus contains a first solvent plug of a chromatographic mobile phase liquid, and said method further comprises, between said aspirating and said transferring steps, the steps of retracting said needle and said intake tube terminus from said container and aspirating into said intake tube a second solvent plug of said chromatographic mobile phase liquid.

10. A method according to claim 9, wherein said switching is fully automated and effected by an algorithm.

11. A method according to claim 9, wherein said aliquot has a volume less than about 100 nl.

12. A method according to claim 7, wherein said aliquot has a volume less than about 100 nl.

* * * * *